United States Patent [19]
Carr et al.

[11] Patent Number: 6,096,891
[45] Date of Patent: Aug. 1, 2000

[54] PROCESS FOR THE PRODUCTION OF CYCLIC N,N'-DIALKYLUREAS

[75] Inventors: Richard V. C. Carr; Kristen Elaine Minnich; John Anthony Marsella, all of Allentown, Pa.

[73] Assignee: Air Products and Chemicals, Inc., Allentown, Pa.

[21] Appl. No.: 09/457,787

[22] Filed: Dec. 9, 1999

[51] Int. Cl.$^7$ ................................................ C07D 239/22
[52] U.S. Cl. .......................................... 544/312; 544/317
[58] Field of Search ...................... 544/312, 317

[56] References Cited

U.S. PATENT DOCUMENTS

| | | | |
|---|---|---|---|
| 4,617,400 | 10/1986 | Ito et al. ................................. | 548/317 |
| 4,864,026 | 9/1989 | Bickert et al. .......................... | 544/315 |
| 4,900,820 | 2/1990 | Kajimoto et al. ....................... | 540/492 |
| 4,918,186 | 4/1990 | Kajimoto et al. ....................... | 540/492 |
| 4,925,940 | 5/1990 | Franz et al. ............................. | 544/315 |

FOREIGN PATENT DOCUMENTS

| | | |
|---|---|---|
| 1173432 | 12/1969 | United Kingdom . |

OTHER PUBLICATIONS

Dehmlow, E. V., et al, "Phase Transfer Catalytic Preparation of the Dipolar Aprotic Solvents DMI and DMPU", *Synthetic Communications*, 18(5), pp. 487–494: 1988.

Polievka, M., et al., "Possibilities of Cyanoethylation of Urea", *Petrochemica*, 12(5), pp. 122–127: 1972.

Halmo, F., et al, "Study of the Product of Cyanoethylation of N,N'–Dimethylolurea Using NMR Spectroscopy", *Petrochemica*, 17(4), pp. 86–92 (1977).

*Primary Examiner*—John M. Ford
*Attorney, Agent, or Firm*—Mark L. Rodgers

[57] ABSTRACT

N,N'-dialkylurea and an α,β-unsaturated nitrile are reacted to form a cyclic N,N'-dialkylurea containing an imine group on a ring carbon. This compound is useful as an intermediate in the formation of N,N'-dialkylpropyleneureas by hydrogenation followed by hydrogenolysis to remove the imine group. Using N,N'-dimethylurea and acrylonitrile as the starting materials one can arrive at N,N'-dimethylpropyleneurea which is a compound useful as an organic solvent and known by its acronym, DMPU.

16 Claims, No Drawings

PROCESS FOR THE PRODUCTION OF CYCLIC N,N'-DIALKYLUREAS

BACKGROUND OF THE INVENTION

This invention relates to a process for the preparation of cyclic N,N'-dialkyl-ureas. In another aspect it relates to a chemical intermediate which can be hydrogenated to form a cyclic dialkylurea. In still another aspect it relates to a two-step method of converting N,N'-dialkylureas to cyclic dialkylureas. In a more specific aspect it relates to a method of making N,N'-dimethylpropyleneurea.

Cyclic N,N'-dialkylureas are valuable as solvents for a variety of organic compounds such as polymers and aromatic hydrocarbons and also as intermediates for the preparation of other solvents and pharmaceuticals. The cyclic urea, N,N'-dimethylpropyleneurea (DMPU) is an excellent polar aprotic solvent that can be used in many applications as a replacement for dimethylformamide (DMF) and hexamethylphosphoramide (HMPA), both of which are suspected carcinogens. The commercial use of DMPU has been severely limited, however, because it has been expensive to produce. There is currently a large market for N-methylpyrrolidone as a replacement for solvents that are possibly carcinogenic. DMPU could help fill that demand if a way could be found to make it at a competitive cost.

Over the last half-century several processes have been developed for the production of these cyclic ureas but none have proven to be successful commercially. As early as 1969 BASF published a British patent, GB 1,173,432, describing the preparation of N,N'-dimethylpropyleneurea and other propyleneureas by the hydrogenolysis of alkoxypropyleneurea. It is stated that prior methods of synthesis have not been commercially attractive because they start with 1,3-propanediamine which is difficult to produce. The process disclosed condenses urea or N-substituted ureas with an unsaturated aldehyde, such as acrolein. The resulting alkoxypropyleneurea is then dissolved in methanol and treated with hydrogen at elevated temperature and pressure in the presence of a Raney nickel catalyst. The hydrogenation removes the alkoxy group leaving only hydrogen or alkyl substituents on the ring.

Other methods of making these cyclic ureas appear to fall into two general groups that can be characterized as follows: (a) those starting with a cyclic urea to which alkyl groups are added to the nitrogen atoms, and (b) those starting with 1,3-propanediamine or dialkylpropanediamine.

Included in the first group (a) is the process disclosed in U.S. Pat. No. 4,617,400, Ito et al. (1986) in which propyleneurea is reacted with formaldehyde under hydrogen pressure of 80 bar, at a temperature of 150° C., and in the presence of a hydrogenation catalyst to make DMPU. Also present is a solid acid made from sulfuric acid and aluminum oxide. The hydrogenation catalysts are reduced nickel or carbon-supported platinum or palladium.

In a 1988 article by Dehmlow and Rao, "Phase Transfer Catalytic Preparation of the Dipolar Aprotic Solvents DMI and DMPU", Synthetic Communications, 18(5), pp. 487–94, a process is described in which a cyclic urea is methylated with dimethylsulfate and potassium carbonate and/or sodium hydroxide. The reactions take place in a solvent such as dioxane or toluene and in the presence of a catalyst such as tetrabutylammonium bromide. The cyclic urea starting material can be made from 1,3-diaminopropane and urea.

U.S. Pat. No. 4,925,940, Franz et al. (1990) describes a process which starts with a cyclic urea that is reacted with formaldehyde to substitute methylol groups on the urea nitrogen atoms. The resulting N,N'-dimethylolpropyleneurea is then hydrogenated under hydrogen pressure of 80 bar, at a temperature of 120° C., and in the presence of a catalyst of palladium supported on an inorganic carrier to make DMPU.

Among the processes which start with 1,3-propanediamine is that disclosed in U.S. Pat. No. 4,864,026, Bickert et al. (1989). In this process the 1,3-propanediamine is reacted with urea to make propyleneurea which is then reacted with formaldehyde and formic acid to add methyl groups onto the ring nitrogen atoms. U.S. Pat. No. 4,900,820, Kajimoto et al. (1990) discloses a process in which urea is reacted with dimethylpropanediamine to form the cyclic urea. In this case the methyl groups are already present on the nitrogen atoms of the propanediamine and are carried forward into the cyclic urea. U.S. Pat. No. 4,918,186, Kajimoto et al. (1990) describes a process which also starts with a symmetrical dimethylpropanediamine in a reaction with phosgene in the presence of sodium hydroxide to make the N, N'dimethyl-substituted cyclic urea.

The processes that rely on symmetrical dimethylpropanediamine as the starting material are not economically practicable because this amine is not commercially available. The processes that use propyleneurea as the starting material require the availability of 1,3-propanediamine as a precursor. This material is relatively expensive because it is made by reacting acrylonitrile with ammonia followed by hydrogenation. Very large excesses of ammonia are required in this reaction in order to minimize the formation of iminobispropionitrile. This by-product has a strong tendency to form because the second addition of acrylonitrile to ammonia is considerably faster than the first addition. Also the hydrogenation conditions of the processes disclosed by the '400 and '940 patents are somewhat severe.

While not directed to the formation of cyclic ureas, an article of interest is one by Polievka et al., "Possibilities of Cyanoethylation of Urea", Petrochemica, 12 (5), pp.122–7 (1972). These authors report attempts to cyanoethylate urea with acrylonitrile that resulted in a mixture of cyanoethylated products which could not be isolated further. The reaction was carried out in a solvent of dimethylsulfoxide in the presence of a basic catalyst. Some polymerization of the acrylonitrile took place, but the cyanoethylated products were thought to be predominantly disubstituted ureas conforming to the formula: NC—$CH_2$—$CH_2$NH—CO—NH$CH_2$—$CH_2$—CN. Other products were said have mono-, tri-, and possibly some tetra-substitution. No cyclic products were reported.

Another similar article is one by Halmo et al., "Study of the Product of Cyanoethylation of N,N'-dimethylolurea Using NMR Spectroscopy", Petrochemica, 17 (4), pp. 86–92. These authors reported results similar to that above with cyanoethylation taking place chiefly at the site of the alcohol groups with some addition occurring on the nitrogen atoms of the methylolurea.

It is apparent from the above review that numerous routes have been proposed for synthesis of DMPU and other cyclic ureas, and that several decades have elapsed during the search for a viable commercial process. There remains, however, the need for an economical method of production that relies upon available starting materials and reaction conditions that are industrially practicable.

SUMMARY OF THE INVENTION

We have discovered that a cyclic N,N'-dialkylurea can be formed by reacting an N,N'-dialkylurea with an α,β- unsaturated nitrile. This reaction, which is carried out in a suitable solvent such as an alkylether and a base catalyst results in the formation of a six-membered heterocyclic ring compound incorporating both the N,N'-dialkylurea and the nitrile moieties with an imine group in the 4-position. This result was quite unexpected in view of the prior literature that describes linear rather than cyclic products when reacting acrylonitrile with urea or N,N'-dimethylolurea. This reaction opens up the possibility of making N,N'-dialkylpropyleneurea in a convenient two-step process that involves first forming the cyclic urea containing the imine group. This compound is a useful chemical intermediate from which the imine group can be removed by hydrogenation, followed by hydrogenolysis either directly or through an intermediate reaction of the amine with an alcohol followed by hydrogenolysis.

In the preferred process N,N'-dimethylurea is reacted with acrylonitrile in the presence of a base catalyst such as sodium hydroxide to form the cyclic urea, N,N'-dimethyldihydrocytosine. This is a six-membered ring compound that carries an imine group on the carbon in the 4-position of the ring. Hydrogenation of this product converts the imine group to an amine group and then removes the amine group by hydrogenolysis, forming ammonia and the desired product, N,N'-dimethylpropyleneurea (DMPU). It is even more preferred to conduct the hydrogenation in the presence of methanol to achieve hydrogenolysis of the N,N'-dimethyldihydrocytosine, converting it to N,N'dimethylpropyleneurea by way of the intermediate formation of 4-methoxy-N,N'-dimethylpropylene urea. This route is favored because it is relatively easy to remove the methoxy group by hydrogenation. In this way the relatively harsh conditions of hydrogenation in the prior art can be avoided.

We have also found that it is very convenient in the production of DMPU by this method to use DMPU as the solvent for the cyclization of urea and the hydrogenation of the resulting product.

DETAILED DESCRIPTION OF THE INVENTION

The economical production of cyclic N,N'-dialkylureas has been an elusive goal for the past several decades, particularly the production of N,N'-dimethylpropyleneurea, known in the art as DMPU, which is an excellent organic solvent. The chemical reaction that we have discovered provides a convenient and cost effective route to this end result using starting materials that are commercially available. These starting materials for the production of DMPU are N,N'-dimethylurea and acrylonitrile.

In general terms the invention has two aspects, the first of which is the production of a cyclic derivative of N,N'-dialkylurea by reaction with an α,β-unsaturated nitrile. The second aspect includes this cyclization reaction but carries it further by hydrogenation followed by hydrogenolysis to form as an end product, N,N'-dialkylpropyleneurea. The starting urea compound is substituted with one alkyl group on each nitrogen atom of the urea molecule. Each nitrogen atom also retains a hydrogen atom. The chemical formula for this starting material can be represented by: RHN—CO—NHR where CO is the carbonyl group and each R is selected from alkyl groups including the aralkyl group, benzyl. These alkyl groups can be straight chain or branched and can have from 1 to 6 carbon atoms, 7 carbon atoms in the case of benzyl. Preferably, the alkyl groups are lower alkyls having 1 to 4 carbons, and methyl is favored most since the dimethyl urea derivative is used in the production of DMPU. These alkyl groups can be the same or different, but symmetrical urea derivatives are preferred because they are the easiest to make.

The α,β-unsaturated nitrile can also be substituted on the α and/or β carbons with alkyl groups as described for the urea derivative. The unsaturated nitrile can be represented by the chemical formula: $R^1{}_2C=CR'—CN$ where each R' is hydrogen or an alkyl group having 1 to 6 carbon atoms. Also, the β carbon can carry an alkoxy group since such a group would be removed during the hydrogenation step that can follow the cyclization of the urea. As with the urea, these R' group substituents on the nitrile can all be the same or different, but it is preferred that the R' groups be either hydrogen or methyl with not over two methyl substituents on the molecule. The most preferred nitrile is acrylonitrile since it is this starting material which is used in the production of DMPU.

The ureidocyclization of the nitrile takes place in a solvent which can be any effective, non-deleterious organic solvent that does not interfere with the reaction, but is preferably an alkylether or DMPU itself. Examples of suitable alkylethers include tetrahydrofuran (THF), dioxane, and the like The reaction is catalyzed with a base which is preferably sodium hydroxide because it is inexpensive and easy to use. Other bases such as potassium hydroxide, tetramethylammonium hydroxide, and the like can be used to catalyze the reaction. The reaction proceeds very well under mild conditions with temperatures from room temperature up to 70° C. and at atmospheric pressure. Preferably the temperature does not exceed 50° C. and this is an appropriate temperature at which to carry out the reaction in a reasonable period of time.

The product of this reaction is the six-membered heterocyclic ring compound that can be represented by the formula:

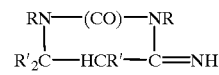

where each R is as described above and each R' group is hydrogen or alkyl, or as described above, one R' on the 6-carbon can be alkoxy. It is preferred that all the R' groups be hydrogen. This compound carries an imine group on the 4-position carbon and it is this imine group that can be removed through hydrogenation to form the N,N'-dialkylpropyleneurea. When the nitrile is acrylonitrile this compound can be referred to as N,N'-dialkyldihydrocytosine. This product precipitates from the solvent on cooling the reaction mixture, for example to room temperature, and any liquid-solid separation such as decanting, filtration or centrifugation can be used to recover the cyclized product.

In a preferred aspect of the invention the ureidocyclization of the nitrile is followed by a hydrogenation or hydrogenolysis which removes the imine group from the product of the ureidocyclization. The hydrogenation process is carried out under hydrogen pressure in the presence of a hydrogenation catalyst. Operable hydrogenation catalysts are well known in the art and a number of such catalysts are suitable. Preferred catalysts include metals of palladium, ruthenium, rhodium, and platinum, used either individually or in combination. Ideally these metals are distributed on an inert support, as is known in the art, and the preferred support is carbon.

The cyclized urea is dissolved in a solvent that can be the same solvent used in the reaction between the urea derivative and the nitrile. DMPU is the favored solvent. The reaction pressure can vary over a broad range and is directly related to the speed of the reaction. In commercial operations the pressure would most likely be determined by the pressure ratings of available equipment and the residence times desired in each case. Generally the pressures can be in the range of 200 psig up to several thousand pounds per square inch. It has been convenient to use about 800 psig for laboratory operations. The temperature of the hydrogenation also affects the rate of reaction and can be in the range of about 40 to as high as 200° C., although our process does not require such severe conditions. Preferred temperatures are more moderate, being in the range of about 50 to 100° C.

In the hydrogenation process ammonia is formed as a byproduct and must be removed to facilitate the reaction going forward, either by venting the ammonia or neutralizing it with acid. Any acid can be used for this purpose but it is preferred to use an organic acid, such as acetic acid. Venting the ammonia or introducing an independent ammonia separation step such as pressure reduction or evaporation saves on the amount of acid required for neutralization, and the choice will depend upon the nature of a commercial operation adapted to this process.

A modification of the hydrogenation process has been found to be advantageous. In this modification, the cyclized urea containing the imine group is hydrogenated in a solvent as described above in the presence of methanol. After conversion of the imine group to an amine group, a small amount of acid is added to catalyze the methanolysis of the amine group to a methoxy group. This alkoxy functional group is more easily cleaved than the amine group on the ring. It was quite unexpected to find that in the presence of a small amount of acid and with the use of a palladium catalyst instead of the nickel or cobalt catalysts mentioned in the patent GB 1,173,432, cited above, the harsh conditions of hydrogenolysis described in the examples of that patent could be avoided. The acid catalyst used in this modification can be one of the acids used for ammonia neutralization, but is preferably an organic acid such as acetic acid.

Following hydrogenation and/or hydrogenolysis of the cyclic urea, the end product is an N,N'-dialkylpropyleneurea that can have up to three alkyl substituents on the 5-position and 6-position carbon atoms in the ring. The preferred end product is DMPU. This product can be recovered from the solvent used in the hydrogenation by cooling to precipitate the solids and using standard solid-liquid separation procedures. Residual solvent can be removed from the recovered product by vaporization, if required, and the crude product can be purified by distillation. DMPU is recovered as a clear liquid.

Other embodiments, advantages and features of the invention will be apparent to those skilled in the art from the following examples which are meant to be illustrative only and should not be construed to limit the invention unduly.

EXAMPLE 1

This example illustrates the preparation of N,N'-dimethyldihydrocytosine. Into a 3-necked round bottomed flask equipped with a pressure equalizing dropping funnel, a reflux condenser, thermometer, and a Teflon-coated magnetic stirring bar was placed 54.7 grams of N,N'-dimethylurea and 100 ml of tetrahydrofuran (THF). The mixture was heated to 50° C. at which point the mixture became homogeneous. Five drops of 50 percent aqueous sodium hydroxide were added to the mixture and 45 ml of acrylonitrile was added over a period of 90 minutes. The mixture was maintained at 50° C. for an additional two hours and was then cooled to ambient temperature. The dark red solvent in the mixture was decanted off and the remaining precipitate was recovered. This precipitate, which was N,N'-dimethyldihydrocytosine, could be used as is without further purification.

EXAMPLE 2

This example illustrates the hydrogenolysis of N,N'-dimethyldihydrocytosine to DMPU by way of the formation of 4-methoxy-N,N'-dimethylpropyleneurea. The N,N'-dimethyldihydrocytosine (0.485 mole) from Example 1 was dissolved in 200 grams of THF and 100 grams of methanol. The catalyst, 10 percent palladium on a carbon support (4.039 g., 50 percent water) and 5 percent rhodium on carbon (4.024 g., 50 percent water) was rinsed three times with THF to remove the water. The N,N'-dimethyldihydrocytosine solution, dried Pd/C, Rh/C, and 5 percent ruthenium on carbon (2.014 g.) and platinum (IV) oxide (1.015 g.) were all charged to a one liter stainless steel autoclave. The reactor was purged three times and leak tested with nitrogen, then hydrogen. The reaction mixture was stirred at room temperature under 54.4 bar (800 psi) of hydrogen for 24 hours. Acetic acid (0.206 mole) was added and the reactor was heated to 60° C. for 48 hours. The reactor was then cooled, vented and emptied and the liberated ammonia was removed from the solution by rotary evaporation at reduced pressure. The product of this reaction was a solution of 4-methoxy-N,N'-dimethylpropyleneurea. This solution was then placed back in the reactor with acetic acid (0.1168 mole) and fresh catalyst prepared as described above. The reactor was heated to 90° C. under 54.4 bar (800 psi) of hydrogen for 48 hours. The reactor was then cooled, vented and the contents filtered. The solvent was removed in vacuo and the crude product was distilled at 1.3 millibar (1 torr) and 90 to 92° C. to give 48.0 g. of N,N'-dimethylpropyleneurea as a clear liquid.

EXAMPLE 3

This example illustrates the hydrogenation of N,N'-dimethyldihydrocytosine to N,N'-dimethylpropyleneurea. Sublimed N,N'-dimethyldihydrocytosine (0.0197 mole), THF (252 g.) and 10 percent Pd/C (0.307 g.) were charged to a one liter pressure reactor. The reactor was purged three times and leak tested with nitrogen and then with hydrogen. The pressure in the reactor was increased to 800 psi with hydrogen and the temperature was raised to 60° C. Reduction to the amine was complete after three hours but there was little N,N'-dimethylpropyleneurea produced. The reactor was cooled and vented and then acetic acid (25 ml) and more Pd/C (1.0406 g.) were added to the reactor. The reactor was sealed, purged and leak tested again. It was then heated to 60° C. and pressurized to 54.4 bar (800 psi) with hydrogen. The amine group had undergone complete hydrogenolysis after three hours and N,N'-dimethylpropyleneurea was formed in 62 percent yield.

Other variations and embodiments of the invention will be apparent to those skilled in the art from the foregoing disclosure and the following claims without departing from the spirit or scope of the invention.

We claim:

1. A process for the production of a cyclic N,N'-dialkylurea which comprises reacting an N,N'-dialkylurea with an α,β-unsaturated nitrile to form a six-membered heterocyclic ring compound incorporating both the N,N'-dialkylurea and the nitrile.

2. The process of claim 1 wherein said ring compound contains an imine group on the ring carbon in the 4-position.

3. The process of claim 1 wherein the alkyl groups in said dialkylurea are individually selected from straight chain and branched alkyls having from 1 to 6 carbon atoms and the aralkyl group benzyl.

4. The process of claim 3 wherein said α,β-unsaturated nitrile contains one to three alkyl substituents on the α and β carbons.

5. The process of claim 1 wherein said dialkylurea is N,N'-dimethylurea and said nitrile is acrylonitrile.

6. The process of claim 1 wherein said reacting is carried out in a reaction media of alkylether.

7. The process of claim 5 wherein said reacting is carried out in a solvent of N,N'-dimethylproplyeneurea.

8. The process of claim 1 which is carried out at a temperature in the range of room temperature to 70° C.

9. The process of claim 1 which is carried out in the presence of a base catalyst.

10. The process of claim 2 in which in a subsequent step said ring compound is subjected to hydrogenation resulting in the reduction of said imine group to an amine group followed by hydrogenolysis of the amine to produce N,N'-dialkylpropyleneurea.

11. The process of claim 10 in which said hydrogenation is carried out in the presence of one or more metallic catalysts selected from palladium, rhodium, ruthenium and platinum.

12. The process of claim 10 wherein methanol is present during the initial hydrogenation of the imine to the amine group replacing said amine group with a 4-methoxy group which is then removed by further hydrogenolysis.

13. The process of claim 12 wherein an acid catalyst in combination with a palladium hydrogenation catalyst is used to promote said hydrogenolysis.

14. The process of claim 13 wherein said acid catalyst is acetic acid.

15. The process of claim 10 wherein said urea is dimethylurea, said nitrile is acrylonitrile, and the product of said hydrogenation is N,N'-dimethylproplyeneurea (DMPU).

16. The process of claim 15 wherein said reaction between said dimethylurea and said acrylonitrile and said hydrogenation are carried out in a solvent of DMPU.

* * * * *